United States Patent [19]

Ghyczy et al.

[11] 4,309,421

[45] Jan. 5, 1982

[54] STABILIZED PARENTERALLY ADMINISTRABLE SOLUTIONS

[75] Inventors: Miklos Ghyczy; Götz Ritzmann; Adorjan Erdös; Eugen Etschenberg, all of Cologne, Fed. Rep. of Germany

[73] Assignee: A. Nattermann & Cie. GmbH, Cologne, Fed. Rep. of Germany

[21] Appl. No.: 139,118

[22] Filed: Apr. 10, 1980

[30] Foreign Application Priority Data

Nov. 4, 1979 [DE] Fed. Rep. of Germany ....... 2914788

[51] Int. Cl.³ .................... A61K 31/19; A61K 31/685
[52] U.S. Cl. ..................................... 424/199; 424/317
[58] Field of Search ................................ 424/317, 199

[56] References Cited

U.S. PATENT DOCUMENTS 3,169,094  2/1965  Wretlind ............................ 424/199

*Primary Examiner*—Stanley J. Friedman
*Attorney, Agent, or Firm*—Burns, Doane, Swecker & Mathis

[57] ABSTRACT

Solutions of anti-inflammatory acrylacetic and arylpropionic acid derivatives are stabilized by addition of phospholipids. The solutions are suitable for parenteral administration; they are well tolerated and have a long-lasting action.

21 Claims, No Drawings

STABILIZED PARENTERALLY ADMINISTRABLE SOLUTIONS

DESCRIPTION

A large number of effective medicaments for the treatment of inflammatory illnesses, such as, for example, rheumatism, have been known for a long time. Since the inflammations are often of a chronic nature, treatment with inflammation-inhibiting medicaments must often take place over a lengthy period. However, the non-steroid anti-inflammatory agents employed for long-term treatment frequently cause symptoms of intolerance, such as ulceration and inflammation of the gastro-intestinal tract, if they are administered orally.

It would therefore be desirable to have available a form for administration of non-steroid anti-inflammatory agents which circumvents the gastro-intestinal tract or does not expose it to locally severe conditions, and which causes the anti-inflammatory action to commence rapidly and last for a long time.

It is known that because of the short half-life of the usual anti-rheumatic medicaments, rheumatic patients must additionally be given sleeping tablets at night, because the duration of action is insufficient. Prolonging the activity through better bio-availability would make it possible to achieve a therapeutic level of action for a longer period (in particular to permit rest at night).

The most important non-steroid antiphlogistics are the arylacetic acid derivatives and arylpropionic acid derivatives. There has therefore hitherto been no lack of attempts to prepare parenterally administrable forms of these substances.

In the form of the free acids, arylacetic acids and arylpropionic acids are insoluble in water. In the form of the alkali metal salts, they exhibit moderate to good solubility in aqueous media. However, these solutions have a pH value greater than 8. Consequently, it has hitherto not been possible to administer these pharmaceutical active ingredients in an inherently desirable parenteral form.

In German Offenlegungsschrift No. 2,730,570, detergents are used to improve with the aid of a micelle-forming agent the solubility of substances which are only sparingly soluble in water (gallic acids).

Attempts have also been made to administer sparingly water-soluble substances in the form of liposomes, cf. German Offenlegungsschriften Nos. 2,818,655, 2,601,207, 2,712,030 and 2,712,031. Here, the active substance is encapsulated in vesicles of phosphatidylcholine and auxiliaries.

Because of the nature of the method of preparation, the yield of encapsulated substance is less than 60%. The non-encapsulated active substance must be separated in an involved manner by physical methods. In preparing the liposomes, chloroform must as a rule be used as the solvent. Since this very toxic solvent forms non-volatile complexes with phosphatidylcholine (M. Okazaki, Chem. Phys. Lipids 1976, 17 (1), 28.7), it is not possible to remove enclosed chloroform from the liposomes.

In addition to the unsafe solvent, cholesterol and stearylamine or phosphatic acid must be employed in addition to phosphatidylcholine in preparing liposomes. Because of the known toxicity of stearylamine and phosphatic acid the parenteral administration of medicaments which contain these substances is not safe.

It has now been found, surprisingly, that arylacetic acid derivatives and arylpropionic acid derivatives such as Ibuprofen (2-(4-isobutylphenyl)-propionic acid), Naproxen (2-(6-methoxy-2-naphthyl)-propionic acid), Aclofenac (4-allyloxy-3-chlorophenylacetic acid), Ketoprofen (2-(3-benzylphenyl)-benzoic acid), Diclofenac (2-(2,6-dichlorophenylamino)-phenylacetic acid), Fenoprofen (2-(3-phenyloxyphenyl)-acetic acid), Tolmetin (1-methyl-5-(p-toluyl)-pyrrol-2-yl-acetic acid), Flurbiprofen (2-(2-fluorobiphenyl-4-yl-propionic acid) and Suprofen (p-2-thenoylhydratropic acid) can be converted into a stable aqueous solution, at a physiological pH, with the aid of phospholipids, without adding further auxiliaries. Novel water-soluble complexes of these acids with the phospholipids are formed. The solutions are exceptionally suitable for parenteral administration (for example intramuscular or intravenous administration) and exhibit a long-lasting inflammation-inhibiting action.

Moreover, these solutions are distinguished not only by excellent tolerance but also by a long-lasting action. In animal experiments, for example, it is found that even 11 hours after a single parenteral administration the action is 3–6 times greater than in the case of a single oral administration of the same dose.

The solution can be prepared by bringing the individual constituents together and homogenising them by stirring in accordance with customary methods. It is not necessary to dissolve one of the constituents beforehand.

A preferred process consists of suspending the arylacetic acid or arylpropionic acid in 10 to 200 parts of water, adding the phospholipid, and stirring vigorously until the mixture is homogeneous. The molar ratio of active substance to phosphatidylcholine in this process is from 1:0.3 to 1:10, ratios from 1:0.3 to 1:0.7, and from 1:3 to 1:7, being particularly preferred.

Before or after the preparation of the homogeneous solutions, additives which render the solutions isotonic, such as sodium chloride, glucose or the like, can be added. It is also advantageous to add a base, such as, for example, sodium hydroxide solution or a buffer, in order to give a pH value which is close to the physiological pH value. The solutions thus prepared can be sterilised, and packed in ampoules, in the usual manner, or can be lyophilised, the resulting dry substance being converted to the desired solution when required. Concentrations of 1–80 mg of active substance per ml can readily be achieved.

Since some of the phospholipids used are sensitive to oxidation and to light, it is advantageous to carry out the process with exclusion of oxygen, under a protective gas atmosphere. Exclusion of light is also advantageous.

Suitable phospholipids are natural and synthetic phospholipids. Suitable natural phospholipids (of vegetable or animal origin) are, in particular, phosphatidylcholine, phosphatidylethanolamine, phosphatidylinositol, phosphatidylserine, spingomyelin, cephalin, lysolecithin, phosphatidylglycol, cardiolipin, plasmalogens, which can be obtained, for example, from soya beans or from egg, and mixtures of these phospholipids, for example the commercially available phosphatidylcholines or phosphatidylcholine mixtures, such as Phospholipon ® 100 (95% pure natural phosphatidylcholine from soya beans);

Phospholipon ® 100H (98% pure fully hydrogenated phosphatidylcholine from soya beans);

Phospholipon ® 80 (phospholipids from soya beans, containing 75% of phosphatidylcholine and 12% of phosphatidylethanolamine); and Phospholipon ® 55 (alcohol-soluble phospholipids from soya beans, containing 55% of phosphatidylcholine).

Examples of suitable synthetic phosphatides are ditetradecanoylphosphatidylcholine, dihexadecanoylphosphatidylcholine, dioleylphosphatidylcholine and dilinolylphosphatidylcholine, and especially dipalmitoylphosphatidylcholine.

The phospholipids have the advantage, over the substances described for this purpose in the literature, that they are substances which occur in the body, are easily degraded in the body, show no side-effects on long-term treatment (see Weihrauch, U.S. Dept. of Agriculture, quoted in the National Enquirer of 6.6.1978, page 33) and themselves do not have any analgesic or anti-inflammatory action.

The solutions prepared in accordance with the present invention are mechanically and chemically very stable. The chemical stability was tested by customary methods, for example by thin layer chromatography. No decomposition was observable on storage at room temperature. The solutions prepared in accordance with the processes described above can also be lyophilised by methods known per se (see, in this context, German patent application No. P 28 5633.9). The lyophilisation gives a dry substance which can very easily be redissolved in water. The shelf life is also very good. Thus, no decomposition was detectable even at 45° C. storage temperature.

The anti-inflammatory activity of the new compositions was determined by the Hillebrecht rat paw oedema test (J. Hillebrecht, Arzneimittelforschung 4, 607 (1954)). In this test, an oedema was produced in one rear paw of rats each weighing 200-250 g by sub-plantar administration of carrageenin (0.5% in 0.9% NaCl solution), using 0.1 ml of solution per paw. After administering the test substance, which as a rule should be in a volume of not more than 10 ml/kg of rat body weight, the volume of the paw is determined by a displacement method. To test the long-term action, the substance was administered 4, 6 and 8 hours before the administration of the carrageenin. The final value is found three hours after administration. At each dosage level, the experiment is carried out with 10 test animals and 10 control animals, all of the same sex, and is repeated with the same number of animals of the other sex. The solutions tested showed a distinct lengthening of action compared with the customary compositions for oral administration.

The following Examples illustrate the invention.

EXAMPLE 1

800 mg of Fenoprofen are suspended in 4 ml of distilled water and the pH is brought to 7 with 1 N NaOH. 1,200 mg of Phospholipon ® 100 are added and the mixture is stirred vigorously until a homogeneous solution results. This is made up to 10 ml with distilled water and again mixed briefly. A virtually colourless solution is obtained.

EXAMPLE 2

800 mg of Tolmetin and 800 mg of Phospholipon 100 are homogenised in 8 ml of distilled water with vigorous stirring. The pH is brought to 6.8 with 1 N NaOH and the mixture is made up to 10 ml with distilled water. A pale yellow solution is obtained.

EXAMPLE 3

The procedure described in Example 2 is followed, but instead of Tolmetin, 800 mg of Naproxen are used.

EXAMPLE 4

The procedure described in Example 2 is followed, but instead of Tolmetin, 800 mg of Ibuprofen are used.

EXAMPLE 5

200 mg of Tolmetin and 2.5 g of Phospholipon 100 are suspended in 50 ml of distilled water and treated, at 40° C., with ultrasonics until a clear solution results.

We claim:

1. A method of treating a subject suffering from an inflammatory illness which comprises administering parenterally to said subject an effective amount of a solution comprising a water-soluble complex of a phospholipid with a non-steroid antiphlogistic comprising an inflammation-inhibiting derivative of an arylacetic or arylpropionic acid selected from the group consisting of 2-(4-isobutylphenyl)-propionic acid, 2-(6-methoxy-2-naphthyl)-propionic acid, 2-(2-fluorobiphenyl-4-yl)-propionic acid, 4-allyloxy-3-chlorophenylacetic acid, 2-(3-benzylphenyl)-benzoic acid, 2-(2,6-dichlorophenylamino)-phenylacetic acid and 2-(3-phenyloxyphenyl)-acetic acid, the molar ratio of said derivative to said phospholipid ranging from about 1:0.3 to 1:10.

2. A method according to claim 1, in which the phospholipid comprises phosphatidylcholine.

3. A method according to claim 1, in which the molar ratio of said derivative to said phospholipid ranges from about 1:3 to 1:7.

4. A method according to claim 1, in which said effective amount ranges from about 1 to 80 milligrams of said derivative per milliliter of solution.

5. A method according to claim 1, in which said derivative comprises 2-(4-isobutylphenyl)-propionic acid.

6. A method according to claim 1, in which said derivative comprises 2-(6-methoxy-2-naphthyl)-propionic acid.

7. A method according to claim 1, in which said derivative comprises 4-allyloxy-3-chlorophenylacetic acid.

8. A method according to claim 1, in which said derivative comprises 2-(3-benzylphenyl)-benzoic acid.

9. A method according to claim 1, in which said derivative comprises 2-(2,6-dichlorophenylamino)-phenylacetic acid.

10. A method according to claim 1, in which said derivative comprises 2-(3-phenyloxyphenyl)-acetic acid.

11. A method according to claim 1, in which said derivative comprises 2-(2-fluorobiphenyl-4-yl)-propionic acid.

12. A parenterally administrable solution comprising a water-soluble complex of a phospholipid with a non-steroid antiphlogistic comprising an inflammation-inhibiting derivative of an arylacetic or arylpropionic acid selected from the group consisting of 2-(4-isobutylphenyl)-propionic acid, 2-(6-methoxy-2-naphthyl)-propionic acid, 2-(2-fluorobiphenyl-4-yl)-propionic acid, 4-allyloxy-3-chlorophenylacetic acid, 2-(3-benzylphenyl)-benzoic acid, 2-(2,6-dichlorophenylamino)- phenylacetic acid and 2-(3-phenyloxyphenyl)-acetic acid, the molar ratio of said derivative to said phospholipid ranging from about 1:0.3 to 1:10.

13. A solution according to claim 12, in which the phospholipid comprises phosphatidylcholine.

14. A solution according to claim 12, in which the molar ratio of said derivative to said phospholipid ranges from about 1:3 to 1:7.

15. A solution according to claim 12, in which said derivative comprises 2-(4-isobutylphenyl)-propionic acid.

16. A solution according to claim 12, in which said derivative comprises 2-(6-methoxy-2-naphthyl)-propionic acid.

17. A solution according to claim 12, in which said derivative comprises 4-allyloxy-3-chlorophenylacetic acid.

18. A solution according to claim 12, in which said derivative comprises 2-(3-benzylphenyl)-benzoic acid.

19. A solution according to claim 12, in which said derivative comprises 2-(2,6-dichlorophenylamino)-phenylacetic acid.

20. A solution according to claim 12, in which said derivative comprises 2-(3-phenyloxyphenyl)-acetic acid.

21. A solution according to claim 12, in which said derivative comprises 2-(2-fluorobiphenyl-4-yl)-propionic acid.

* * * * *

UNITED STATES PATENT AND TRADEMARK OFFICE
CERTIFICATE OF CORRECTION

PATENT NO. : 4,309,421
DATED : January 5, 1982
INVENTOR(S) : MIKLOS GHYCZY et al It is certified that error appears in the above-identified patent and that said Letters Patent are hereby corrected as shown below:

The Foreign Application Priority Data on the first page of the patent which reads "Nov. 4, 1979 [DE] Federal Republic of Germany.....2914788"

should read instead

--April 11, 1979 [DE] Federal Republic of Germany....2914788--.

Signed and Sealed this

Twenty-seventh Day of March 1984

[SEAL]

Attest:

GERALD J. MOSSINGHOFF

Attesting Officer   Commissioner of Patents and Trademarks